United States Patent
Walker et al.

[11] Patent Number: 6,144,867
[45] Date of Patent: Nov. 7, 2000

[54] SELF-PIERCING PULSE OXIMETER SENSOR ASSEMBLY

[75] Inventors: Steven C. Walker, Olmos Park; John M. Shepherd, Fort San Antonio, both of Tex.

[73] Assignee: The United States of America as represented by the Secretary of the Army, Washington, D.C.

[21] Appl. No.: 09/389,347

[22] Filed: Sep. 3, 1999

Related U.S. Application Data

[60] Provisional application No. 60/101,142, Sep. 18, 1998.
[51] Int. Cl.[7] .................................................. A61B 5/00
[52] U.S. Cl. ............................................ 600/340; 600/344
[58] Field of Search .................................. 600/340, 344, 600/322, 323, 310

[56] References Cited

U.S. PATENT DOCUMENTS

| | | |
|---|---|---|
| 3,908,665 | 9/1975 | Moses . |
| 4,270,531 | 6/1981 | Blachly et al. . |

(List continued on next page.)

FOREIGN PATENT DOCUMENTS

| | | |
|---|---|---|
| 4 42 260A1 | 5/1996 | Germany . |
| WO 86/00207 | 1/1986 | WIPO . |
| WO 90/01293 | 2/1990 | WIPO . |
| WO 90/07907 | 7/1990 | WIPO . |
| WO 6/29927 | 10/1996 | WIPO . |
| WO 96/31155 | 10/1996 | WIPO . |
| WO 97/42903 | 11/1997 | WIPO . |

OTHER PUBLICATIONS

Hayes, et al., "Quantitative Investigation of Artefact in Photoplethysmography and Pulse Oximetry for Respiratory Exercise Testing," Aug. 27, 1998, Web Article: http://www.lut.ac.uk/departments/el/research/optics/ppgraphy/paper2c.htm.

Anonymous, "Photon Flow For Pulse Oximetry," Sep. 15, 1995, Web Article: http://www.llnl.gov/bbrp/healthcare/projects/pfpulseoxim.html.

Heathgate Data Corp., "Pulse Oximetry," Jun. 13, 1997, Web Article: http://www.healthgate.com/healthgate/free/dph/static/dph.0200.shtml.

Jobes, et al., "Monitoring of Arterial Hemoglobin Oxygen Saturation Using a Tongue Sensor," Anesthesia & Analgesia, Feb., 1988, vol. 67, pp. 186–188.

O'Leary, et al., "Buccal Pulse Oximeter Is More Accurate Than Finger Pulse Oximeter in Measuring Oxygen Saturation," Anesthesia & Analgesia, Oct., 1992, vol. 75, pp. 495–498.

(List continued on next page.)

OTHER PUBLICATIONS

Cote, et al., "Tongue Oximetry in Children with Extensive Thermal Injury: Comparison with Peripheral Oximetry," Can. Journal Anaesth., May, 1992, vol. 39, Issue 5, pp. 454–457.

Reynolds, et al., "Influence of Sensor Site Location on Pulse Oximetry Kinetics in Children," Anesthesia & Analgesia, 1993, vol. 76, pp. 751–754.

Faisst, et al., "Reflectance Pulse Oximetry in Neonates," European Journal of Obstetrics & Gynecology and Reproductive Biology, Aug., 1995, vol. 61, pp. 117–122.

*Primary Examiner*—Cary O'Connor
*Assistant Examiner*—Catherine McPherson
*Attorney, Agent, or Firm*—Elizabeth Arwine; Charles H. Harris

[57] ABSTRACT

A self-piercing pulse oximeter sensor is provided for attachment to subject, e.g., an individual or an animal. The device includes a flexible pulse oximeter sensor, an earring post, and a grommet. The earring post may be used as a piercing device if there is not a pierced body part suitable for attaching the pulse oximeter sensor to the body. Otherwise the earring post may be slid into the pierced hole. In either case, the tip of the earring post engages a grommet once passing through the body part. Thus, the pulse oximeter sensor functions in a transilluminance mode by transmitting light through the pierced body part.

20 Claims, 1 Drawing Sheet

U.S. PATENT DOCUMENTS

| | | |
|---|---|---|
| 4,495,945 | 1/1985 | Liegner . |
| 4,586,513 | 5/1986 | Hamaguri . |
| 4,621,643 | 11/1986 | New, Jr. et al. . |
| 4,624,572 | 11/1986 | Van Den Bosch . |
| 4,651,746 | 3/1987 | Wall . |
| 4,676,240 | 6/1987 | Gardy . |
| 4,700,708 | 10/1987 | New, Jr. et al. . |
| 4,796,636 | 1/1989 | Branstetter et al. . |
| 4,830,014 | 5/1989 | Goodman et al. . |
| 4,854,699 | 8/1989 | Edgar, Jr . |
| 4,859,057 | 8/1989 | Taylor et al. . |
| 4,867,557 | 9/1989 | Takatani et al. . |
| 4,880,304 | 11/1989 | Jaeb et al. . |
| 5,040,539 | 8/1991 | Schmitt et al. . |
| 5,069,214 | 12/1991 | Samaras et al. . |
| 5,203,329 | 4/1993 | Takatani et al. . |
| 5,205,281 | 4/1993 | Buchanan . |
| 5,217,012 | 6/1993 | Young et al. . |
| 5,246,003 | 9/1993 | Delonzor . |
| 5,282,464 | 2/1994 | Brain . |
| 5,329,922 | 7/1994 | Atlee, III . |
| 5,355,874 | 10/1994 | Bertram . |
| 5,357,954 | 10/1994 | Shigezawa et al. . |
| 5,361,757 | 11/1994 | Smith et al. . |
| 5,413,101 | 5/1995 | Sugiura . |
| 5,417,207 | 5/1995 | Young et al. . |
| 5,494,032 | 2/1996 | Robinson et al. . |
| 5,595,176 | 1/1997 | Yamaura . |
| 5,596,986 | 1/1997 | Goldfarb . |
| 5,673,693 | 10/1997 | Solenberger . |
| 5,678,544 | 10/1997 | Delonzor et al. . |
| 5,715,816 | 2/1998 | Mainiero et al. . |
| 5,743,261 | 4/1998 | Mainiero et al. . |
| 5,797,841 | 8/1998 | Delonzor et al. . |
| 5,800,349 | 9/1998 | Isaacson et al. . |
| 5,817,009 | 10/1998 | Rosenheimer et al. . |
| 5,839,439 | 11/1998 | Nierlich et al. . |
| 5,991,648 | 11/1999 | Levin ...................................... 600/344 |

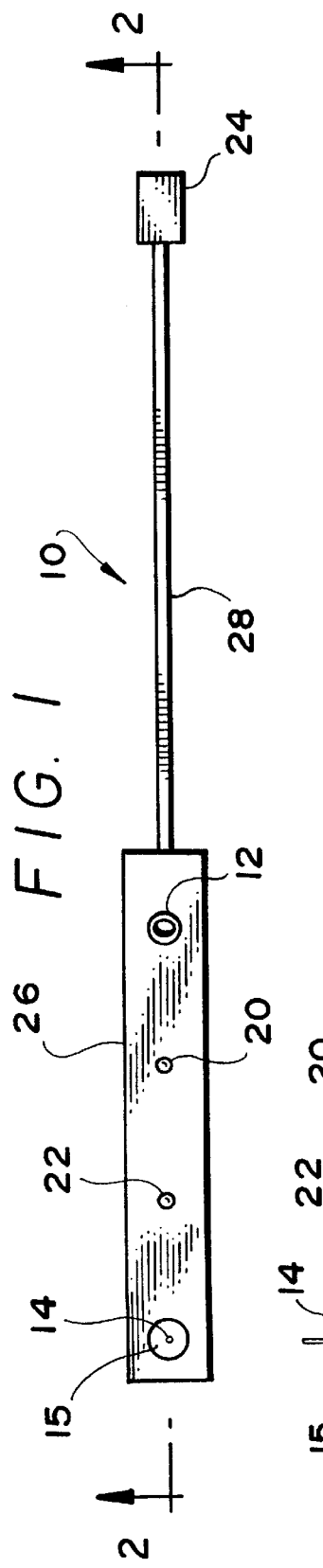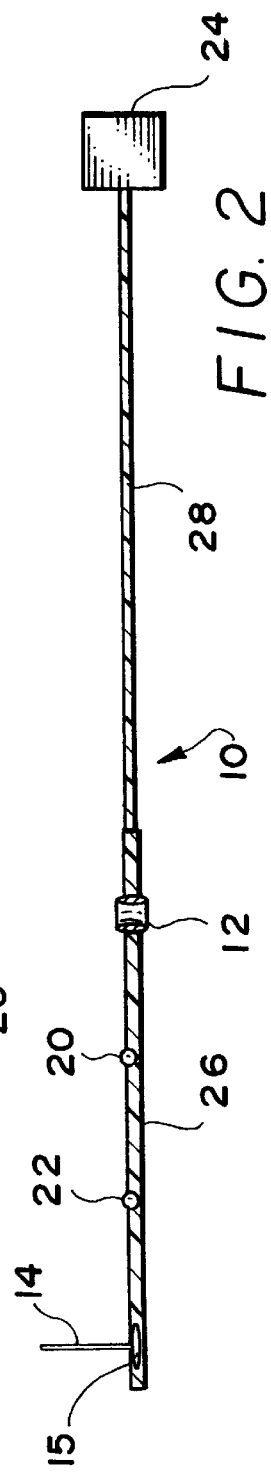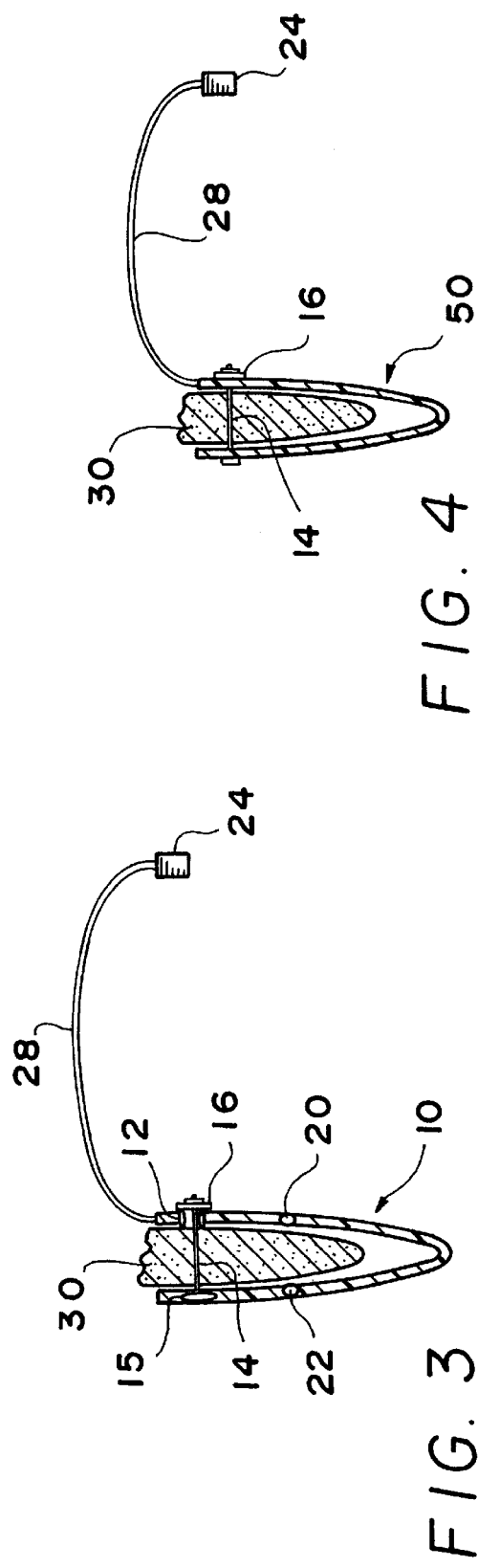
FIG. 1
FIG. 2
FIG. 3
FIG. 4

SELF-PIERCING PULSE OXIMETER SENSOR ASSEMBLY

This application claims priority from U.S. provisional application Ser. No. 60/101,142, filed Sep. 18, 1998.

I. FIELD OF THE INVENTION

The invention relates to transillumination pulse oximetry. More particularly, the invention is directed to a self-piercing pulse oximeter sensor capable of attachment to either an individual or an animal through a pierced body part.

II. BACKGROUND OF THE INVENTION

Prior pulse oximeter sensors have been attached to an appendage of an individual such as a patient. A flexible pulse oximeter sensor is usually placed on a finger or toe of a patient who is in need of medical monitoring, with tape or a plastic clamp. The pulse oximeter sensor may also be taped to the ear or held in place on the ear with a plastic clamp. Attaching the pulse oximeter sensor to the ear usually occurs in a case where the patient is missing his/her digits, e.g., an amputee, or severely injured, or in the case of significant burns covering the body such that the placement of the pulse oximeter sensor on a peripheral body part is very difficult. However, monitoring via the ear is presently tenuous at best, as the methods of securing a pulse oximeter sensor to the ear are haphazard and unreliable.

Furthermore, there are times when a patient will need to move while having a pulse oximeter sensor attached. An example of this is when a wounded soldier needs to remain in battle gear with his/her hands free to fight and/or operate equipment while being monitored. Other examples are laboratory testing or monitoring of the physiological status of an individual or moving a patient under field conditions as in battle or EMS activities. The present pulse oximeter sensors are attached in such away as to prevent this freedom of activity and movement.

Notwithstanding the usefulness of the above-described pulse oximeter sensors, a need still exists for placement of a pulse oximeter sensor so that it will be secure with little risk of coming off of patients who have no sites for secure placement in the traditional fashion. Furthermore, a pulse oximeter sensor is needed that is capable of attachment to an individual who needs to have his/her extremities free of monitoring devices.

III. SUMMARY OF THE INVENTION

This invention solves the ongoing problems of attaching a pulse oximeter sensor to a patient who needs freedom of movement and/or lacks suitable sites for attachment. The invention while addressing the problems of the prior art obtains advantages that were not achievable with the prior art devices.

In accordance with one aspect of the invention, a pulse oximeter sensor is provided which is attachable to pierced body parts, like pierced ear lobes. The invention may also be attached through a new piercing from its non-reactive puncture post.

An object of this invention is to provide a stronger more fixed attachment of a pulse oximeter sensor to an individual.

A further object of this invention is to provide flexibility in terms of where a pulse oximeter sensor is attached to an individual based on available body parts for attachment.

Still another object of this invention is to attach a pulse oximeter sensor to an individual while allowing optimal freedom of movement for the individual.

An advantage obtained by this invention is enhanced physical stability between the pulse oximeter sensor and the individual making it possible for better quality recordings of data signals and thereby better patient care.

Another advantage obtained by the invention is that it provides a more reliable mechanism for taking oximetry measurements on animals.

In accordance with an aspect of the invention, a pulse oximeter assembly is provided. The pulse oximeter assembly includes a pulse oximeter sensor including a flexible base and an aperture passing therethrough. A post provided with a sharp point may be connected to the pulse oximeter sensor. The point of the post should be sharp enough to pierce the flesh of a subject. A grommet is disposed on the flexible base to frame the aperture.

In accordance with another aspect of the invention, a pulse oximeter assembly is provided. The pulse oximeter assembly includes a flexible pulse oximeter sensor which comprises a flexible base, a hole passing through the flexible base, a light source disposed on the flexible base, a light detector disposed on the flexible base, and a connector coupled to the light source and the light detector. A post having a shaft extending through the flexible base is provided to facilitate attachment of the pulse oximeter assembly to a subject's desired body part. A grommet is disposed on the flexible base, such that the grommet frames the hole passing through the flexible base.

IV. DESCRIPTION OF THE DRAWINGS

FIG. 1 illustrates a top view of the pulse oximeter assembly of the present invention.

FIG. 2 illustrates a cross-section of the pulse oximeter assembly shown in FIG. 1 taken at line 2—2.

FIG. 3 illustrates a cross-section of the pulse oximeter assembly shown in FIG. 1 attached to an ear lobe.

FIG. 4 illustrates another embodiment of the pulse oximeter assembly of the present invention.

V. DETAILED DESCRIPTION OF THE INVENTION

FIGS. 1–3 illustrate a preferred embodiment of the self-piercing pulse oximeter sensor assembly 10. The self-piercing pulse oximeter assembly 10 includes a grommet 12, an earring post 14, a light source 20, and a light detector 22; each of these is connected to a flexible base 26. More particularly, the light source 20 and the light detector 22 may be disposed on an outer surface of the flexible base 26 or disposed within the flexible base 26. A connector 24 may be coupled to flexible base 26 through cabling 28. The term earring post is used simply as a convenience to describe a piercing structure. However, this structure is not limited to connection to an ear lobe, but the device may be attached to a variety of body parts of a subject such as a person or an animal.

Examples of the flexible pulse oximeter suitable for this invention are shown in U.S. Pat. Nos. 4,621,643 and 4,700,708 and embodied by the Nellcor® Oxysensor® II D-25. The light source 20 preferably is one or more of the following: a light emitter, a bispctral emitter, a dual spectral emitter, a photoemitter, two light emitting diodes (LED), a photodiode, or a semiconductor die. However, any light source that facilitates reflectance pulse oximetry may be employed. When the light source 20 is one light emitter then the light emitter, for example, would emit two frequencies of light at about 660 nm and about 940 nm. Typically, a two emitter arrangement will include a red LED near 660 nm and a near-infrared LED emitting in the range of 890 to 950 nm. The light source 20 may emit light having a bandwidth in the range of 20 to 50 nm.

The light detector 22 detects light emitted by light source 20. Electrical signals representing the detected light through the connector 24 to a spectrophotometer or pulses oximeter that discriminates between the relative intensity of these emissions and provides an index as to the degree of oxygen saturation of hemoglobin in blood. The light detector 22 may be one of the following devices: a photoelectric receiver, a photodetector, a photodiode, or a semiconductor die.

The connector 24 preferably includes contact electrodes, conductive lines and a cord. The light source 20 and the light detector 22 are each connected to a respective contact electrode. The conductive lines connect the contact electrodes to the cord. The cord connects to a spectrophotometer.

In keeping with the invention, the flexible pulse oximeter sensor may be attached to the earring post 14. The earring post 14 may be threaded through a subject's ear lobe thus facilitating attachment of the pulse oximeter assembly 10 to a subject's ear as illustrated in FIG. 3. The earring post 14 is preferably manufactured from non-physiologically reactive materials such as metal or plastic. The earring post 14 may be mounted on a flat thin base 15 that stabilizes the earring post 14 preferably at right angles with respect to the flexible pulse oximeter sensor. The base 15 may be incorporated within the flexible base 26. Preferably, the flat base 15 is also made of non-physiologically reactive materials.

The earring post 14 may be capable of piercing a body part 30 of the subject if a pre-pierced body part is not available or is deemed insufficient for engagement. The earring post 14 preferably has a sharp tip that provides the piercing capability. In accordance with a preferred aspect of the invention, the earring post 14 may be sufficiently sharp to pierce an ear lobe, the webbing between fingers or toes, the foreskin, the tongue, the nose, eyebrows, breast nipples, the cheek/lip, etc. One of ordinary skill in the art will realize that other parts of the body beyond those listed could be pierced sufficiently to allow for transillumination pulse oximetry. If the webbing is chosen for piercing, then preferably the webbing between the thumb and the forefinger on one hand is pierced. Furthermore, if piercing of a body part is not required, then the earring post 14 may readily slide through the previously pierced hole.

The grommet 12 reinforces a hole or eyelet made in and through the flexible pulse oximeter sensor. The grommet 12 engages and holds the tip of the earring post 14 after the earring post 14 is placed through and in the selected body part of the subject being monitored. The grommet 12 and the earring post 14 preferably are at or near opposite ends of flexible base 26.

After the pulse oximeter sensor is no longer needed for monitoring, the grommet 12 may be disengaged from the earring post 14 and the earring post 14 may be removed from the body part. As a result, the self-piercing pulse oximeter may be worn, put on, and/or removed in a manner similar to an earring that a person might wear for decoration.

To strengthen the connection between the grommet 12 and the earring post 14, an earring-securing piece 16 may be attached to the earring post 14 after it passes through the grommet 12 as shown in FIG. 3. Preferably, the earring-securing piece 16 may be made of either plastic or nonreactive metal. A suitable earring-securing piece 16 may be a standard earring-securing piece that is typically found on off-the-shelf pierced earrings. The earring-securing piece 16 may also be incorporated into the grommet 12 as a single securing device.

Another embodiment of the invention is illustrated in FIG. 4. The pulse oximeter sensor includes an earring post 14, a flexible pulse oximeter 50, and an earring-securing piece 16. The flexible pulse oximeter 50 includes a light source 20, a light detector 22, and a connector 24.

The flexible pulse oximeter 50 may be wrapped around the body part through which the transillumination is to occur such that when attached the earring post 14 passes through the two ends of the flexible pulse oximeter 50 and the body part. In this embodiment, the earring post 14 is then either pierced through the flexible pulse oximeter 50 and the body part or simply pressed through the flexible pulse oximeter 50 into a previously pierced body part. The earring-securing piece 16 is attached to the earring post 14 to attach the flexible pulse oximeter 50 to the body part and thus the individual.

This invention may be used in patient populations where monitoring is difficult such as field injury or illness, severely burned patients, multiple amputees or astronauts/pilots/soldiers/workers who need extremities free to perform certain activities like fighting or controlling/operating a vehicle or machinery. This invention may also be used to monitor healthy persons while they work, fight, or perform other activities for health status surveillance. This invention may also find uses in the veterinary sciences for monitoring oxygen levels in animals, which monitoring would encounter similar problems as that with monitoring humans.

The preferred uses allow the pulse oximeter assembly to be firmly attached to the subject without fear of it becoming dislodged during transport and/or movement by the subject wearing the pulse oximeter sensor. The versatility in attaching the pulse oximeter assembly will allow its use by special operations soldiers, pilots, astronauts, divers and other similar professionals while they carry out their duties to allow monitoring of the local tissue oxygen saturation.

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

We claim:

1. A pulse oximeter assembly comprising:
   a flexible pulse oximeter sensor including a flexible base having a hole passing therethrough,
   a post connected to said pulse oximeter sensor, said post including a sharp point such that said sharp point is capable of piercing flesh, and
   a grommet in communication with said pulse oximeter sensor, said grommet framing the hole passing through said pulse oximeter sensor.

2. The pulse oximeter assembly according to claim 1, wherein said post includes a base disposed within said pulse oximeter sensor.

3. The pulse oximeter assembly according to claim 1, wherein said post includes a non-reactive material selected from a group cosisting of a metal and plastic.

4. The pulse oximeter assembly according to claim 1, wherein said post includes an earring post.

5. The pulse oximeter assembly according to claim 1, wherein said flexible pulse oximeter sensor includes:
   at least one light source,
   at least one light detector in communication with said at least one light source, and a connector connected to said at least one light source and said at least one light detector.

6. The pulse oximeter assembly according to claim 5, wherein said light source includes one of at least one light emitter, a bispectral emitter, a dual spectral emitter, at least one photoemitter, at least one photodiode, at least one light emitting diode, and a semiconductor die.

7. The pulse oximeter assembly according to claim 5, wherein said at least one light detector includes one of a photoelectric receiver, a photodetector, a photodiode receiver, and a semiconductor die.

8. The pulse oximeter assembly according to claim 1, wherein said post is disposed near one end of the flexible base and said grommet is disposed near the other end of the flexible base.

9. The pulse oximeter assembly according to claim 1, further comprising an earring-securing portion capable of engaging said post.

10. The pulse oximeter assembly according to claim 1, wherein said grommet includes an earring-securing portion capable of engaging said post.

11. A method for using the pulse oximeter assembly according to claim 1, said method comprising:
   placing the post through a subject's body part,
   engaging the post with the grommet of the pulse oximeter sensor, and
   connecting the pulse oximeter sensor to another device.

12. The method according to claim 11, further comprising piercing the subject's body part with the sharp point of the shaft.

13. A pulse oximeter assembly comprising:
   a flexible pulse oximeter sensor having:
      a flexible base,
      a hole passing through the flexible base,
      a light source connected to the flexible base,
      a light detector connected to the flexible base, and
      a connector coupled to the light source and the light detector;
   a post having a shaft extending from the flexible base; and
   a grommet in communication with the flexible base, the grommet framing the hole passing through the flexible base.

14. The pulse oximeter assembly according to claim 13, wherein the shaft includes a sharp point capable of piercing a body part of a subject.

15. The pulse oximeter assembly according to claim 13, wherein the post is disposed at one end of the flexible base and the grommet is disposed at the other end of the flexible base.

16. The pulse oximeter assembly according to claim 13, further comprising an earring-securing element capable of engaging the post.

17. The pulse oximeter assembly according to claim 13, wherein the light source includes at least one of at least one light emitter, a bispectral emitter, a dual spectral emitter, at least one photoemitter, at least one photodiode, at least one light emitting diode, and a semiconductor die.

18. The pulse oximeter assembly according to claim 13, wherein the light detector includes one of a photoelectric receiver, a photodetector, a photodiode receiver, and a semiconductor die.

19. A method for using the pulse oximeter assembly according to claim 13, said method comprising:
   placing the shaft through a subject's body part,
   engaging the shaft with the grommet of the pulse oximeter sensor, and
   connecting the pulse oximeter sensor to another device.

20. The method according to claim 19, further comprising piercing the subject's body part with the sharp point of the shaft.

* * * * *